US00PP22634P2

(12) United States Plant Patent
Zlesak

(10) Patent No.: US PP22,634 P2
(45) Date of Patent: Apr. 10, 2012

(54) *PHYSOCARPUS* PLANT NAMED 'DONNA MAY'

(50) Latin Name: *Physocarpus opulifolius*
Varietal Denomination: Donna May

(76) Inventor: David Charles Zlesak, St. Paul, MN (US)

( * ) Notice: Subject to any disclaimer, the term of this patent is extended or adjusted under 35 U.S.C. 154(b) by 278 days.

(21) Appl. No.: 12/657,271

(22) Filed: Jan. 19, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

| | | | | |
|---|---|---|---|---|
| PP11,211 | P * | 2/2000 | Kordes et al. | Plt./226 |
| PP14,821 | P2 * | 5/2004 | Wood | Plt./226 |
| PP18,660 | P2 * | 3/2008 | Tuite | Plt./226 |

OTHER PUBLICATIONS

UPOV ROM GTITM Computer Database, GTI OUVE Retrieval Software 2011, Citation for 'Donna May'.*
Shinn, Meghan. 2011 Intros from Bailey Nurseries "Horticulture the Art and Science of Smart Gardening" Nov. 20, 2010 available at: http://www.hortmag.com/plants/2011-intros-from-bailey-nurseries.*

* cited by examiner

*Primary Examiner* — Wendy C Haas

(57) ABSTRACT

'Donna May' is a new and distinct cultivar of *Physocarpus opulifolius* having an upright, mounded, dense plant habit; compact overall plant size; strong branching characteristics; small foliage size; short internode length; purple foliage color throughout the growing season; corymbs of small flowers with pink petals; and ability to root and grow vigorously from softwood and semi-hardwood cuttings.

5 Drawing Sheets

Latin name of the plant claimed: *Physocarpus opulifolius*.
Variety denomination: 'Donna May'.

BACKGROUND OF THE INVENTION

The present invention relates to a new and distinct cultivar of *Physocarpus opulifolius* and will be referred to hereafter by its cultivar name, 'Donna May'. *Physocarpus opulifolius* is a deciduous shrub grown for landscape use. The primary objective of the *Physocarpus opulifolius* breeding program I initiated in St. Paul, Minn. was to develop a new *Physocarpus opulifolius* cultivar that possessed the purple foliage color of *Physocarpus opulifolius* 'Monlo' (disclosed in U.S. Plant Pat. No. 11,211) and the compact, well-branched growth habit and small foliage of *Physocarpus opulifolius* var. *nanus* (not patented).

'Donna May' originated by crossing an unnamed *Physocarpus opulifolius* seedling (code designation of this seeding is 2001-1) as the female parent and an unknown plant of *Physocarpus opulifolius* var. *nanus* as the male parent. 2001-1 originated from a cross I made between *Physocarpus opulifolius* 'Monlo' (disclosed in U.S. Plant Pat. No. 11,211) as the female parent and an unknown plant of *Physocarpus opulifolius* var. *nanus* as the male parent. 2001-1 has purple foliage and a growth habit and foliage size intermediate to its parents. The pollination that led to the population of progeny that 'Donna May' was identified within occurred in June 2004. The seeds of this population germinated during the winter of 2004/2005 indoors under florescent lights. Seedlings were transplanted to an outdoor garden bed in St. Paul, Minn. in spring of 2005 and 'Donna May' was selected as a single plant from the population of progeny during the summer of 2005. 'Donna May' was first asexually propagated using semi-hardwood cuttings in the fall of 2005. I have found that the characteristics of 'Donna May' are stable and true to type over successive generations of vegetative propagation.

'Donna May' was unique from all other *Physocarpus* seedlings because of its dark purple foliage color, very compact, well-branched plant habit, and small foliage. These traits led to it being chosen as an advanced selection in the summer of 2005 and asexually propagated for the first time in the fall of 2005. When 'Donna May' first flowered in 2006 it was discovered that 'Donna May' also possesses attractive flowers with pink petals that contrast nicely with the foliage.

SUMMARY OF THE INVENTION

The primary objective of the breeding project was substantially achieved, along with other desirable improvements, as evidenced by the following unique combination of characteristics that are outstanding in the new variety and that distinguish it from its parents, as well as from all other varieties of *Physocarpus opulifolius* of which I am aware:

1. Upright, mounded, dense plant habit;
2. Compact overall plant size;
3. Strong branching characteristics;
4. Small foliage size;
5. Short internode length;
6. Purple foliage color throughout the growing season;
7. Corymbs of small flowers with pink petals;
8. Ability to root and grow vigorously from softwood and semi-hardwood cuttings.

Asexual reproduction of this new cultivar by rooting softwood and semi-hardwood cuttings, as performed at St. Paul, Minn. and Cottage Grove, Minn., shows that the foregoing and all other characteristics and distinctions come true to form and are established and transmitted through succeeding propagations.

Comparison with Parents

'Donna May' has a more compact overall plant size with a denser plant habit than 2001-1. In addition, compared to 2001-1, 'Donna May' branches much more freely, has smaller leaves and flowers, and also has shorter internodes. 'Donna May' and 2001-1 share the traits of purple foliage color and pink petal color. 'Donna May' differs from its male parent, *Physocarpus opulifolius* var. *nanus*, in that 'Donna May' has purple foliage color versus green foliage color, darker pink petal color, and a slightly more compact overall plant size. 'Donna May' and *Physocarpus opulifolius* var. *nanus* are similar in that they both have strong branching characteristics, a dense plant habit, small foliage, small flowers, and short internodes.

Comparison of 'Donna May' with Similar Cultivars

The *Physocarpus opulifolius* cultivars with the greatest similarity to 'Donna May' are 'Lady in Red' (disclosed in U.S. Plant Pat. No. 18,660) and 'Seward' (disclosed in U.S. Plant Pat. No. 14,821). Both 'Lady in Red' and 'Seward' grow to be larger at maturity than 'Donna May' in overall plant size and leaf and flower size. Both 'Lady in Red' and 'Seward' also have longer internodes than 'Donna May'. 'Lady in Red' and 'Seward' are also not as strongly branched and do not have as dense of plant habit as 'Donna May'. For instance, four-year-old plants of 'Donna May' in St. Paul, Minn. in outdoor field plots grew to approximately 1 m tall, while plants of the same age of 'Seward' growing in St. Paul, Minn. were approximately 2 m tall.

BRIEF DESCRIPTION OF THE DRAWINGS

The accompanying colored photographs illustrate the overall appearance of 'Donna May'. The photographed plants were four-years-old in the 2009 growing season, the growing season when the photographs were taken. These plants were propagated from semi-hardwood cuttings. Photographed plants were growing outdoors within the Twin Cities Metro area in Minn. (Arden Hills, Cottage Grove, and Edina, Minn.). Photographs show the colors as true as it is reasonably possible to obtain with colored reproductions of this type. Colors in the photographs may differ from the color values cited in the detailed botanical description which accurately describe the colors of 'Donna May'.

DETAILED BOTANICAL DESCRIPTION

Figure 1:
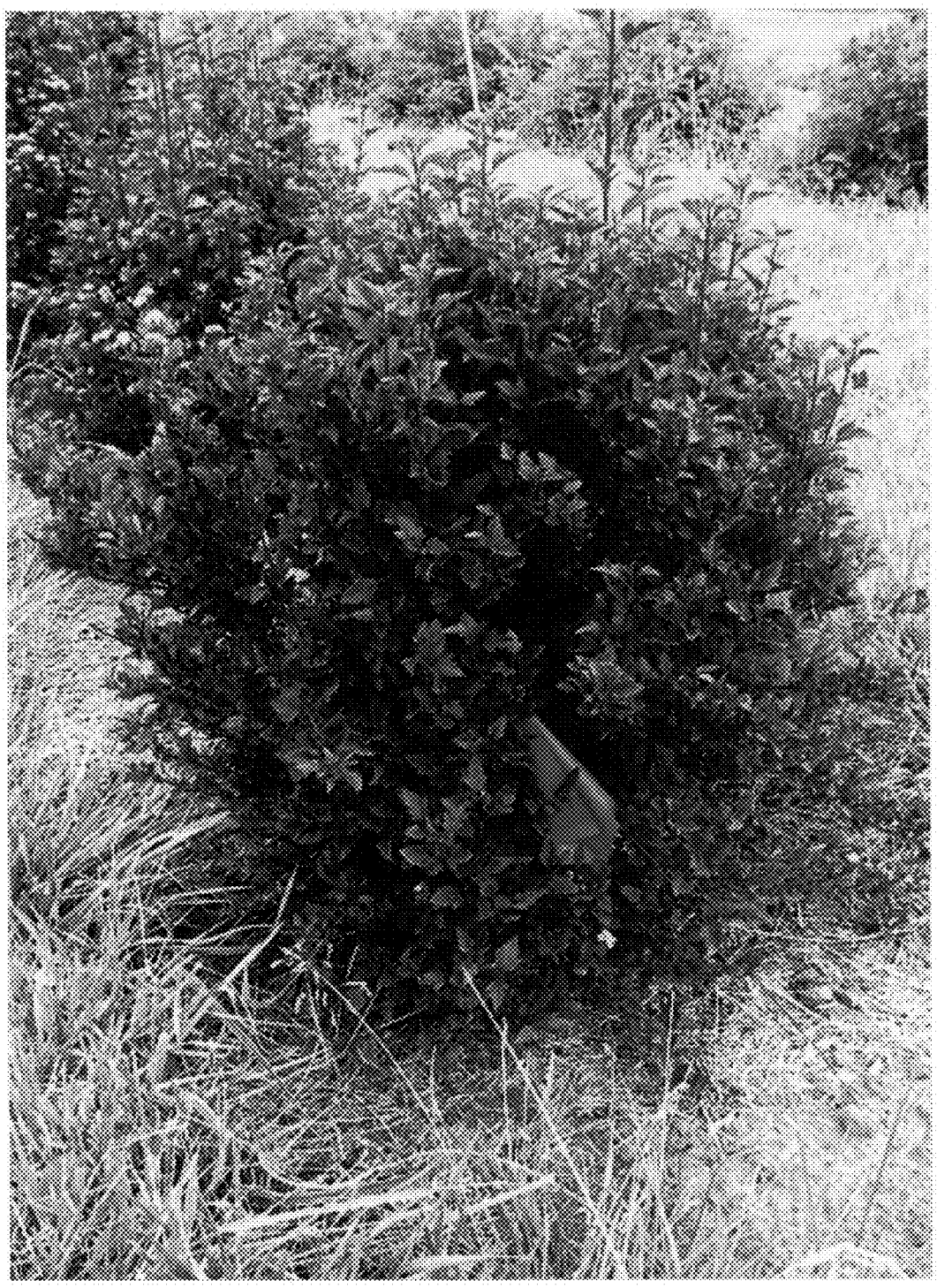
FIG. 1 illustrates a plant of 'Donna May' growing in an open field in full sun in June 2009.
Figure 2:
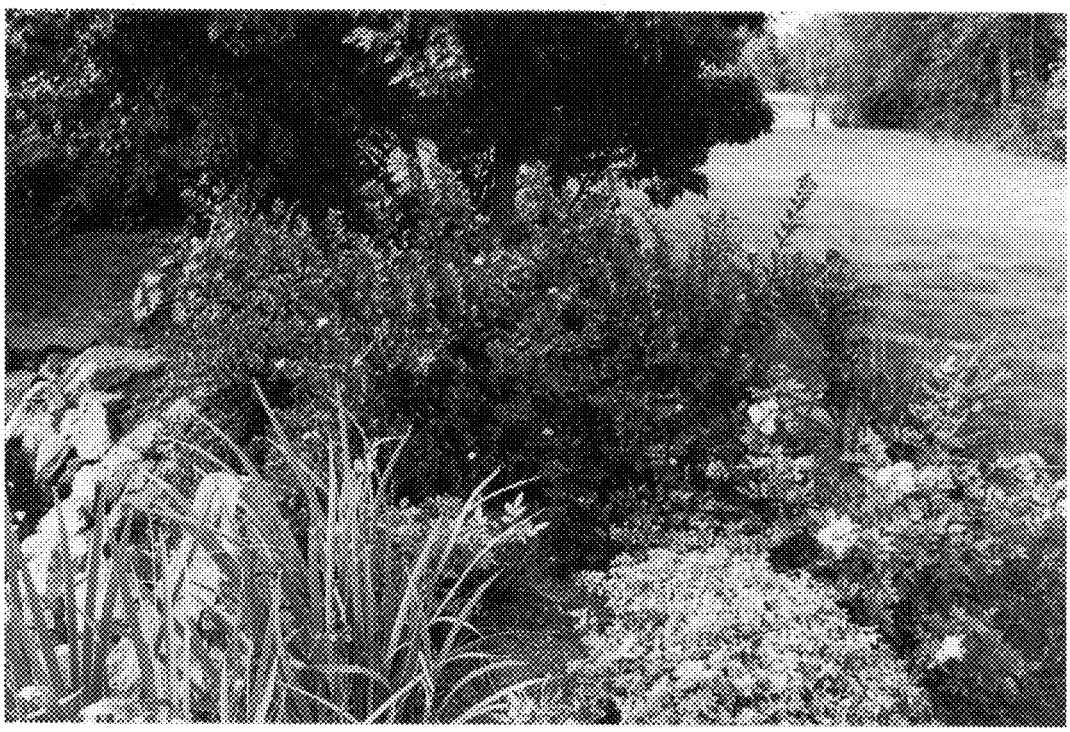
FIG. 2 illustrates two plants of 'Donna May' growing in partial sun in a landscape with other woody plants in September 2009.
Figure 3:
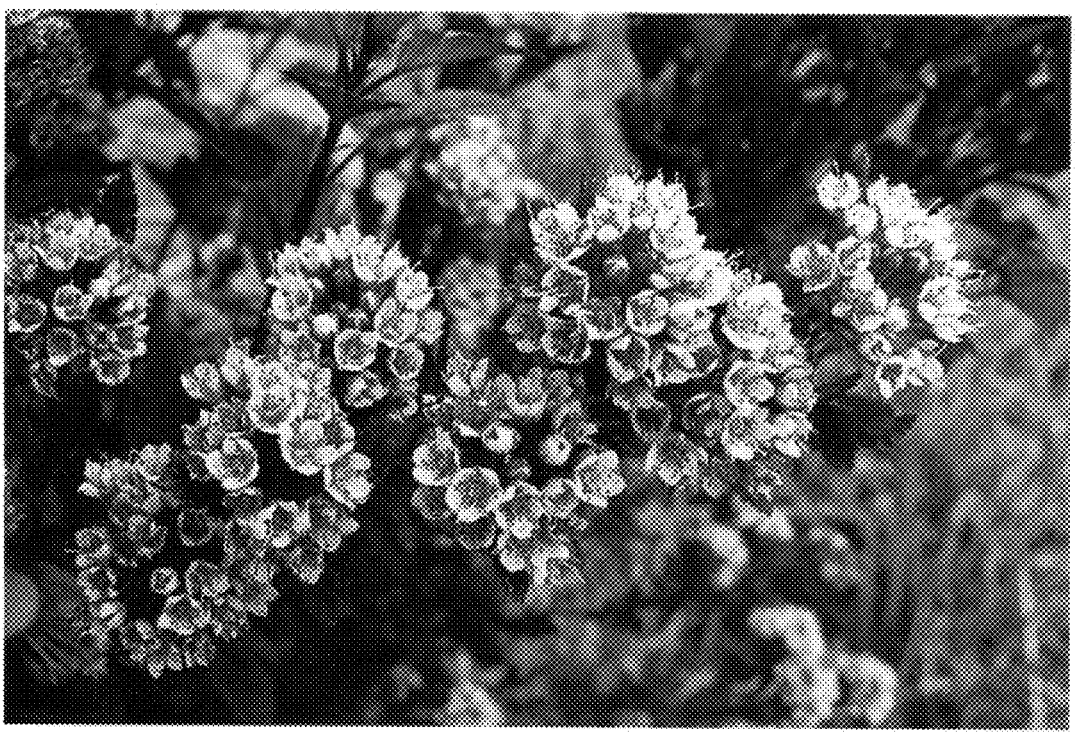
FIG. 3 illustrates corymbs of flowers of 'Donna May' in mid-June 2009.
Figure 4:
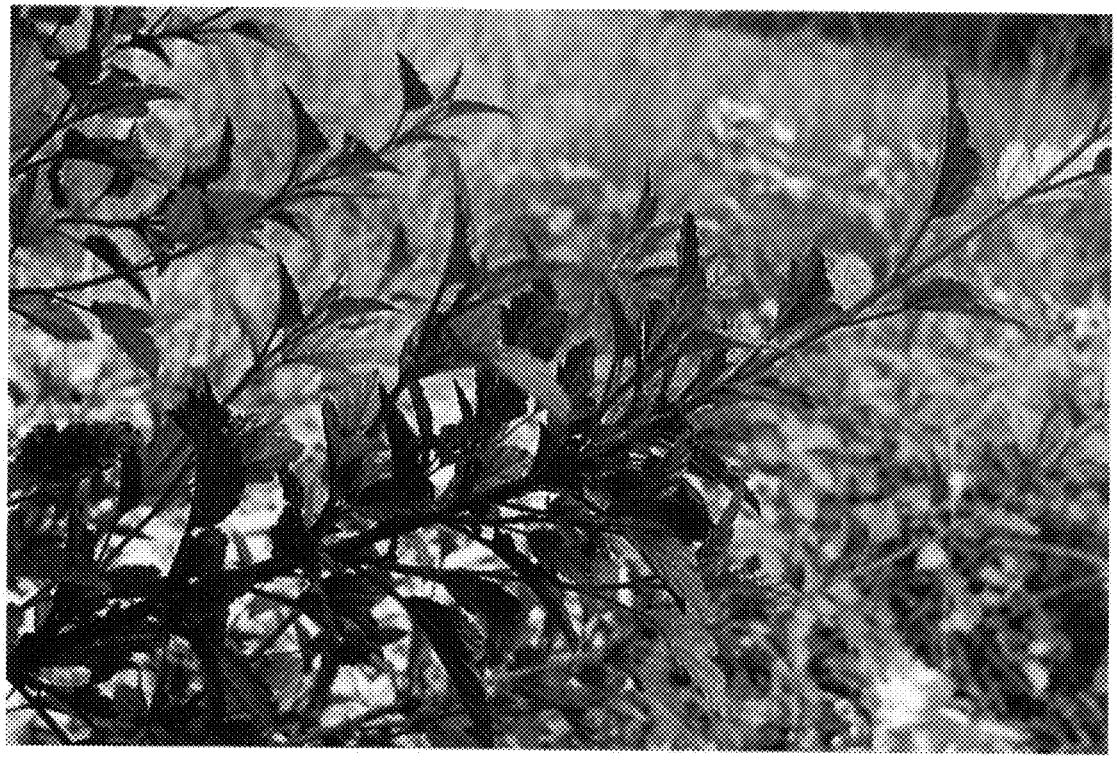
FIG. 4 illustrates the strongly branching habit of current season's growth of 'Donna May' in August 2009.
Figure 5:
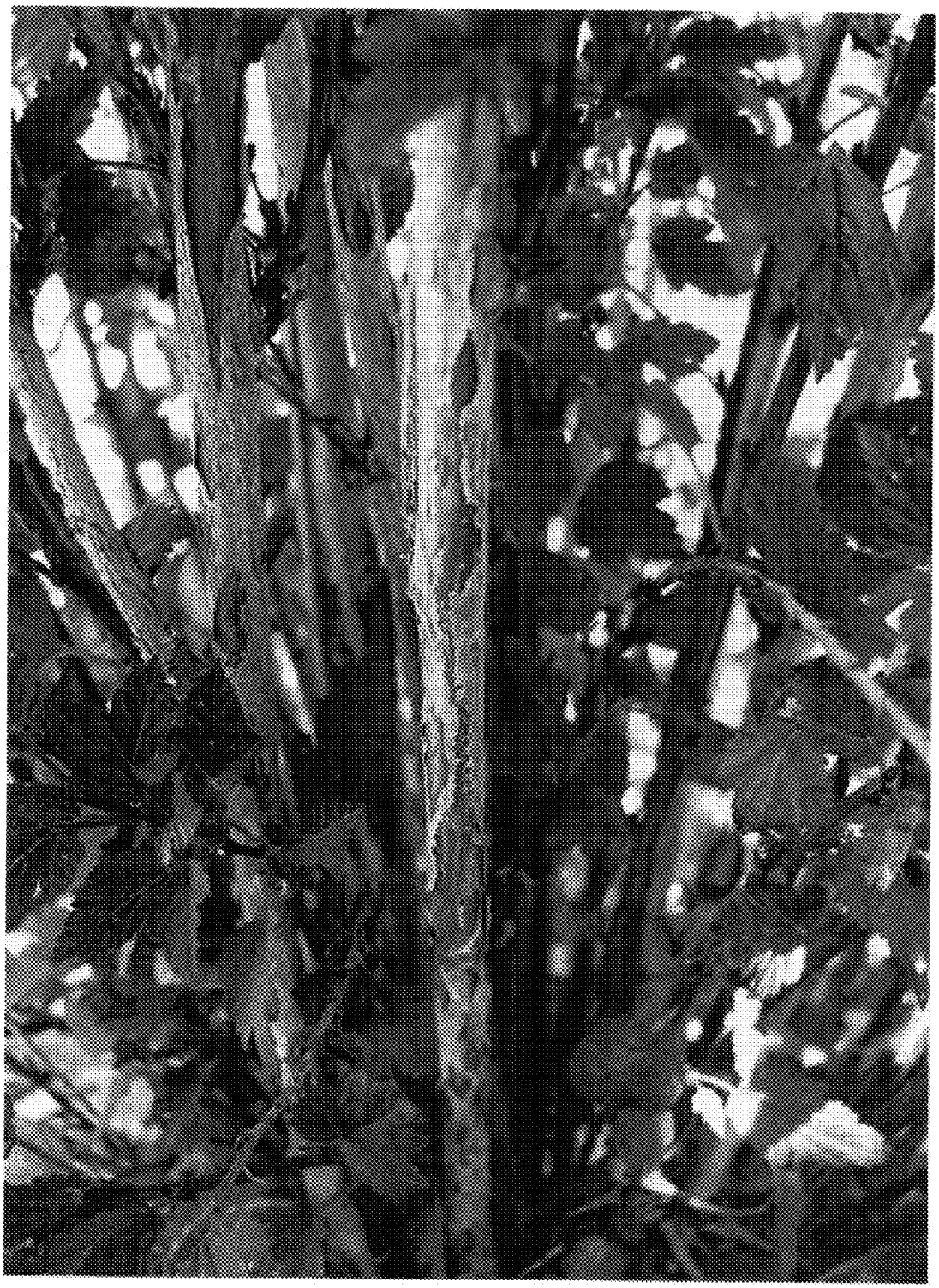
FIG. 5 illustrates stems at the base of a plant of 'Donna May' with exfoliating bark.
Figure 6:
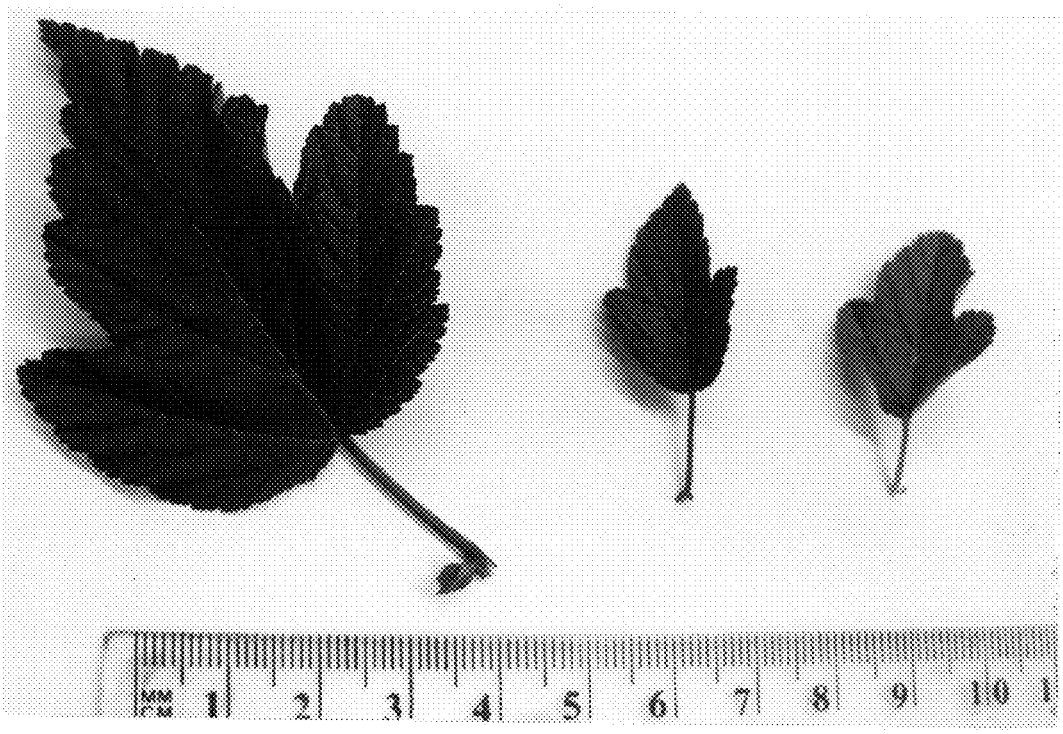
FIG. 6 illustrates representative leaves of 2001-1 (male parent of 'Donna May'; left side of illustration), 'Donna May' (middle leaf in illustration), and *Physocarpus opulifolius* var. *nanus* (female parent of 'Donna May'; right side of illustration).

The following is a detailed description of 'Donna May', the new *Physocarpus opulifolius* cultivar, with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. Descriptions are based on observations of four-year-old plants propagated from stem cuttings and growing in Arden Hills, Cottage Grove, and Edina, Minn.

Classification:

*Botanical.*—*Physocarpus opulifolius* 'Donna May'.

*Common name of species.*—*Physocarpus* or ninebark.

*Commercial.*—Deciduous shrub.

Parentage:

*Seed parent.*—An unreleased seedling selection designated 2001-1. 2001-1 originated from a cross I made of *Physocarpus opulifolius* 'Monlo' (disclosed in U.S. Plant Pat. No. 11,211) as the female parent and *Physocarpus opulifolius* var. *nanus* as the male parent. 2001-1 was selected from a seedling population because it has purple foliage and a growth habit and foliage size intermediate to its parents.

*Pollen parent.*—*Physocarpus opulifolius* var. *nanus* (not patented).

General description:

*Plant habit.*—Upright, mounded, and compact.

*Plant size.*—1.0-1.2 m in overall height and width.

*Growth habit.*—Vigorous and dense with very strong branching characteristics.

*Blooming period.*—About 21 days from mid June to early July.

*Hardiness.*—Cold hardy to USDA Zone 3.

*Root description.*—Fibrous and vigorous.

*Diseases and pest resistance.*—No susceptibility or resistance to diseases or pests known to effect *Physocarpus opulifolius* have been observed for 'Donna May'.

*Cultural requirements.*—'Donna May' does well in full to partial sun and well-drained, moderately fertile soil.

Growth and propagation:

*Propagation.*—Softwood and semi-hardwood stem cuttings have been effective.

*Time required for root initiation and initial development.*—It takes about 3 to 4 weeks during the summer using intermittent mist in the greenhouse without supplemental lighting for cuttings to generate roots.

*Time required to obtain a well-rooted cutting.*—It takes about 6 to 7 weeks to produce a well-rooted cutting in a 2 inch container.

Branch description:

*Branch color.*—The color of current season stems is Greyed-Purple Group 183A. The most mature stems on four-year-old plants had a mixture of colors on the exfoliating bark; primarily Greyed-Orange Group 165C, but there were also areas of Greyed-Orange Group 165A, Greyed-Orange Group 165B, Greyed-Orange Group 165D and White Group N155A.

*Branch size.*—Branches produced during the current season of growth ranged from approximately 15 cm to 60 cm in length and 1 to 4 mm in width. The oldest branches on four-year plants were up to 1.5 cm in diameter at the base of the plant.

*Branch surface.*—Glabrous, smooth, slight sheen.

*Internode length.*—1.5 to 2.0 cm.

*Branch habit*.—Primarily densely foliaged basal branches, potential for lateral branches any node if pruned.

Foliage description:

*Leaf size*.—Overall leaf length is up to about 4.0 cm (average 3.75 cm) and 1.0-1.25 cm wide (average 1.2 cm).

*Leaf division*.—Simple.

*Leaf attachment*.—Petiolate.

*Leaf arrangement*.—Alternate.

*Leaf number*.—It varies, but an actively growing branch can easily produce 30-60 leaves in a growing season.

*Leaf blade shape*.—Ovate in overall leaf blade outline with three prominent lobes.

*Leaf blade base*.—Rounded to slightly cordate.

*Leaf blade apex*.—Acute.

*Leaf blade venation*.—Primary venation is palmate with three principal veins. Each principal vein diverges at the juncture of the leaf blade and petiole and travels through to the middle of a primary lobe. Secondary venation off of the three principal veins is pinnate.

*Leaf blade margin*.—The three primarily lobes have secondary undulations or lobes. The margin on the three primary lobes is best described then as doubly serrate.

*Leaf blade surface*.—Glabrous on upper and lower surfaces.

*Leaf blade size*.—The leaf blade is approximately 2.5-2.75 cm long and 1.0-1.25 cm wide.

*Leaf blade color*.—Young emerging leaf blades are Greyed-Purple Group 183A on the upper and lower surfaces. Young expanded leaf blades are Greyed-Purple Group 187A on the upper surface and most of the lower surface except for veins on the lower surface are Greyed-Green Group 191A. Mature leaves are Greyed-Purple Group 187A on the upper surface and Greyed-Green Group 191A throughout the lower surface.

*Petiole size*.—About 1.0-1.25 cm in length and about 1 mm in width.

*Petiole shape*.—Sulcate. The petiole is generally round except for a longitudinal furrow running the length of the upper surface.

*Petiole color*.—Greyed-Purple Group 183C.

*Petiole texture*.—Glabrous.

*Stipule number*.—There are two stipules at each node with one on each side of the leaf petiole where it attaches to the stem.

*Stipule size*.—2-3 mm long and 1.25 mm wide.

*Stipule shape*.—Generally lanceolate.

*Stipule color*.—Greyed-Purple Group 183A.

Flower description:

*Inflorescence type*.—A corymb with 15-25 rotate flowers arranged in a hemisphere.

*Inflorescence size*.—Typically 1.5-2.0 cm in height and width.

*Inflorescence lastingness*.—The corymb has open flowers typically for up to 21 days with each individual flower open for approximately 3 days.

*Flower bud shape*.—Elliptic.

*Flower bud size and proportions*.—2.5-3.0 mm in length and 2.0 mm in width. The receptacle of the bud accounts for about two-thirds of the proximal end and the calyx accounts for about a third of the distal end of the unopened flower bud.

*Flower bud color*.—The overall color can best be described as Orange Red Group N34C. The overall base color is green and it is overlaid with red.

*Flower size when fully open*.—4.0-5.0 mm in diameter and 4.0 mm in depth (not including peduncle).

*Flower fragrance*.—Slight.

*Petal number*.—5.

*Petal size*.—2.5-3.0 mm in length and width.

*Petal shape*.—Elliptic to obovate.

*Petal color*.—Expanding petals are White Group N155B on the upper surface and White Group N155C on the lower surface. Fully expanded petals are White Group N155B on both the upper and lower surfaces.

*Sepal number*.—5.

*Sepal size*.—Length is 3.0 mm and width is 1.5-2.0 mm.

*Sepal shape*.—Deltoid.

*Sepal color*.—Orange Red Group N34C.

*Peduncle size*.—About 1.0 cm in length and 1.0 mm in diameter.

*Peduncle color*.—Orange Red Group N34C. Green overlaid with red and relatively consistent in color.

*Subtending bract size*.—There is a subtending bract where each peduncle meets the central stem of the corymb. The subtending bract is 2.0-3.0 mm long and 1 mm wide below the peduncles at the proximal end of the corymb to 1.0-1.25 mm long and 0.75-1.0 mm wide for the more distal peduncles at the terminal of the corymb.

*Subtending bract shape*.—Elliptic to obovate.

*Subtending bract color*.—Orange Red Group N34C.

Gynoecium:

*Pistil number per flower*.—Typically there are 4, but sometimes 3.

*Stigma shape*.—Globular.

*Stigma size*.—0.25 mm.

*Stigma color*.—Yellow Green Group 146D.

*Style shape*.—Linear.

*Style size*.—About 4 mm long and 0.2 mm wide.

*Style color*.—Yellow Group 145D.

*Ovary shape*.—Elliptic.

*Ovary size*.—About 0.3 mm.

*Ovary color*.—Yellow Green Group 145C with portions of Red Purple Group 73B overlaid.

Androecium:

*Stamen number per flower*.—Approximately 25.

*Anther shape*.—Elliptic to round.

*Anther size*.—0.5 mm.

*Anther color*.—Red Group 53A.

*Pollen color*.—Red Group 53A.

*Filament shape*.—Linear.

*Filament size*.—1.0-3.0 mm long and 0.1-0.2 mm wide.

*Filament color*.—Yellow Group 145D.

Fruit and seeds:

*Fruit*.—There are typically three or four firm-walled follicles that form per flower. Follicles split along both sides of the seam, but split more readily along the inner or adaxial seam. Follicles are elongated and generally ovate in shape with acuminate tips. They are up to 8.0 mm long and approximately 2.0 mm wide and range in color from Greyed-Purple Group 183A to Greyed-Green Group 193A. Follicle color tends to be green when out of direct sunlight and increasingly purple the more direct sunlight received.

*Seeds per follicle*.—There are up to 2 seeds per follicle.

*Seed shape*.—Ovate.

*Seed size*.—Up to about 2.0 mm long and 1.25 mm wide.

*Seed color*.—Developing seed is typically Greyed-Yellow Group 161B. Mature seed color is between Greyed-Orange Group 164D and Greyed-Orange Group 165D.

I claim:

1. A new and distinct cultivar of *Physocarpus opulifolius* plant substantially as herein shown and described, characterized particularly by its upright, mounded, dense plant habit; compact overall plant size; strong branching characteristics; small foliage size; short internode length; purple foliage color throughout the growing season; corymbs of small flowers with pink petals; and ability to root and grow vigorously from softwood and semi-hardwood cuttings.

* * * * *